United States Patent [19]

Green

[11] Plant 4,819

[45] Feb. 2, 1982

[54] EARLY COLORING SPUR-TYPE RED DELICIOUS APPLE TREE

[75] Inventor: Lester Green, Wenatchee, Wash.

[73] Assignee: Wells & Wade Fruit Co., Inc., Wenatchee, Wash.

[21] Appl. No.: 19,873

[22] Filed: Mar. 12, 1979

[51] Int. Cl.[3] ..... A01H 5/03

[52] U.S. Cl. ..... Plt./35

[58] Field of Search ..... Plt./35

[56] References Cited

U.S. PATENT DOCUMENTS

P.P. 4,372 1/1979 Craig ..... Plt./35

*Primary Examiner*—Robert E. Bagwill

*Attorney, Agent, or Firm*—Christensen, O'Connor, Johnson & Kindness

[57] ABSTRACT

An earlier coloring mutation of Oregon Spur apple, which ripens substantially therewith.

No Drawings

1

My present invention relates to a new and distinct variety of apple tree discovered by me as a sport limb growing on a red delicious apple tree in the Twin W Orchard of Wells & Wade Fruit Co., Inc. near Orondo, Douglas County, Wash. The parent tree of the new variety is the spur-type red delicious tree referred to as "Oregon Spur", U.S. Plant Pat. No. 2,816.

The new variety is substantially indistinguishable from its parent variety except it colors approximately ten days ahead of the parent Oregon Spur trees in the same orchard. The new variety is substantially indistinguishable from the Craig mutation (U.S. Plant Pat. No. 4,372) of Oregon Spur except that its fruit ripens, as does that of its parent, approximately one week later than that of Craig. Successive generations of trees of the new variety have been asexually reproduced. Comparative observations of these successive generations of trees of the new variety and of the parent trees growing in proximity to each other in different locations have confirmed that this early fruit coloration characteristic

2 of the new variety is fixed and comes true to form in successive generations. As an example observation, fruit of the new variety was observed on Aug. 3, 1978 to have more than 50% of its surface area showing red coloration, whereas the fruit on adjacent trees of the parent variety showed red coloration over less than 3% of the surface area.

Inasmuch as the new variety is otherwise substantially identical with the parent variety and inasmuch as the coloration of the fruit of the variety, despite its earlier occurrence, is the same as that of the parent variety stage for stage during ripening, drawings or photographs showing the new variety are not necessary.

I claim:

1. A new and distinct variety of apple tree substantially identical with its parent "Oregon Spur", U.S. Plant Pat. No. 2,816, except it colors approximately ten days ahead of the parent variety.

* * * * *